United States Patent
Nagel et al.

(10) Patent No.: US 12,408,662 B2
(45) Date of Patent: *Sep. 9, 2025

(54) HYDROGEN PEROXIDE AND PERACID STABILIZATION WITH MOLECULES BASED ON A PYRIDINE CARBOXYLIC ACID

(71) Applicant: ECOLAB USA INC., Saint Paul, MN (US)

(72) Inventors: Chris Nagel, Saint Paul, MN (US); Junzhong Li, Saint Paul, MN (US); Keith G. LaScotte, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/675,717

(22) Filed: May 28, 2024

(65) Prior Publication Data

US 2024/0306637 A1    Sep. 19, 2024

Related U.S. Application Data

(63) Continuation of application No. 16/548,356, filed on Aug. 22, 2019, now Pat. No. 12,058,999.

(60) Provisional application No. 62/721,162, filed on Aug. 22, 2018.

(51) Int. Cl.
| | |
|---|---|
| *A01N 25/22* | (2006.01) |
| *A01N 37/16* | (2006.01) |
| *A01N 59/00* | (2006.01) |
| *A23B 2/758* | (2025.01) |
| *A23B 2/771* | (2025.01) |
| *A61L 2/00* | (2006.01) |
| *A61L 2/18* | (2006.01) |
| *C02F 1/50* | (2023.01) |
| *C02F 103/36* | (2006.01) |

(52) U.S. Cl.
CPC ............. *A01N 25/22* (2013.01); *A01N 37/16* (2013.01); *A01N 59/00* (2013.01); *A23B 2/758* (2025.01); *A23B 2/771* (2025.01); *A61L 2/0088* (2013.01); *A61L 2/186* (2013.01); *C02F 1/50* (2013.01); *A23V 2002/00* (2013.01); *A61L 2202/23* (2013.01); *C02F 2103/365* (2013.01)

(58) Field of Classification Search
None
See application file for complete search history.

(56) References Cited

U.S. PATENT DOCUMENTS

| | | |
|---|---|---|
| 2,363,778 A | 11/1944 | Pedersen |
| 2,609,391 A | 9/1952 | Greenspan |
| 2,624,655 A | 1/1953 | Greenspan |
| 2,663,621 A | 12/1953 | Greenspan |
| 2,953,572 A | 9/1960 | Dunn |
| 2,955,905 A | 10/1960 | Davies |
| 3,048,624 A | 8/1962 | Dunn |
| 3,053,633 A | 9/1962 | Dunlop |
| 3,130,169 A | 4/1964 | Blumbergs |
| 3,140,149 A | 7/1964 | Habernickel |
| 3,156,654 A | 11/1964 | Konecny |
| 3,168,554 A | 2/1965 | Phillips |
| 3,192,254 A | 6/1965 | Hayes |
| 3,192,255 A | 6/1965 | Cann |
| 3,256,198 A | 6/1966 | Matzner |
| 3,272,750 A | 9/1966 | Chase |
| 3,432,546 A | 3/1969 | Oringer |
| 3,442,937 A | 5/1969 | Sennewald |
| 3,847,830 A | 11/1974 | Williams |
| 3,925,234 A | 12/1975 | Hachmann |
| 3,956,159 A | 5/1976 | Jones |
| 3,969,258 A | 7/1976 | Carandang |
| 4,003,841 A | 1/1977 | Hachmann |
| 4,013,575 A | 3/1977 | Castrantas |
| 4,051,058 A | 9/1977 | Bowing |
| 4,051,059 A | 9/1977 | Bowing |
| 4,100,095 A | 7/1978 | Hutchins |
| 4,126,573 A | 11/1978 | Johnston |
| 4,129,517 A | 12/1978 | Eggensperger |
| 4,144,179 A | 3/1979 | Chatterji |
| 4,170,453 A | 10/1979 | Kitko |
| 4,233,235 A | 11/1980 | Camden |
| 4,297,298 A | 10/1981 | Crommelynck |
| 4,367,156 A | 1/1983 | Diehl |

(Continued)

FOREIGN PATENT DOCUMENTS

| | | |
|---|---|---|
| WO | 9115474 A1 | 10/1991 |
| WO | 9410284 A1 | 5/1994 |

(Continued)

OTHER PUBLICATIONS

Ecolab USA Inc., in connection with PCT/US2019/047614 filed Aug. 22, 2019, "The International Search Report and the Written Opinion of the International Searching Authority, or the Declaration", 15 pages, mailed Nov. 25, 2019.

(Continued)

*Primary Examiner* — Alton N Pryor

(74) *Attorney, Agent, or Firm* — McKee, Voorhees & Sease, PLC

(57) ABSTRACT

Stabilized peroxycarboxylic acid compositions are provided. The stable peroxycarboxylic acid compositions are particularly suitable for use in sanitizing equipment and surfaces to reduce yeasts, spores and bacteria, including those having contact with food, food products and/or components thereof, which require or benefit from infection control suitable for direct contact with such food sources are provided.

16 Claims, 4 Drawing Sheets

(56) References Cited

U.S. PATENT DOCUMENTS

| | | |
|---|---|---|
| 4,370,251 A | 1/1983 | Liao |
| 4,374,035 A | 2/1983 | Bossu |
| 4,391,723 A | 7/1983 | Bacon |
| 4,391,724 A | 7/1983 | Bacon |
| 4,412,934 A | 11/1983 | Chung |
| 4,473,507 A | 9/1984 | Bossu |
| 4,483,778 A | 11/1984 | Thompson |
| 4,486,327 A | 12/1984 | Murphy |
| 4,529,534 A | 7/1985 | Richardson |
| 4,587,264 A | 5/1986 | Jourdan-Laforte |
| 4,588,506 A | 5/1986 | Raymond |
| 4,617,090 A | 10/1986 | Chum |
| 4,655,781 A | 4/1987 | Hsieh |
| 4,681,592 A | 7/1987 | Hardy |
| 4,778,618 A | 10/1988 | Fong |
| 4,783,278 A | 11/1988 | Sanderson |
| 4,853,143 A | 8/1989 | Hardy |
| 4,879,057 A | 11/1989 | Dankowski |
| 4,917,815 A | 4/1990 | Beilfuss |
| 4,957,647 A | 9/1990 | Zielske |
| 4,964,870 A | 10/1990 | Fong |
| 5,019,292 A | 5/1991 | Baeck |
| 5,030,240 A | 7/1991 | Wiersema |
| 5,073,285 A | 12/1991 | Liberati |
| 5,098,598 A | 3/1992 | Sankey |
| 5,143,641 A | 9/1992 | Nunn |
| 5,196,133 A | 3/1993 | Leslie |
| 5,200,189 A | 4/1993 | Oakes |
| 5,250,212 A | 10/1993 | De Buzzaccarini |
| 5,250,707 A | 10/1993 | Inaba |
| 5,266,587 A | 11/1993 | Sankey |
| 5,296,239 A | 3/1994 | Colery |
| 5,310,774 A | 5/1994 | Farrar |
| 5,314,687 A | 5/1994 | Oakes |
| 5,349,083 A | 9/1994 | Brougham |
| 5,382,571 A | 1/1995 | Granger |
| 5,431,849 A | 7/1995 | Damhus |
| 5,435,808 A | 7/1995 | Holzhauer |
| 5,447,648 A | 9/1995 | Steindorf |
| 5,453,214 A | 9/1995 | Van Den Berg |
| 5,463,112 A | 10/1995 | Sankey |
| 5,464,563 A | 11/1995 | Moore |
| 5,466,825 A | 11/1995 | Carr |
| 5,472,619 A | 12/1995 | Holzhauer |
| 5,486,212 A | 1/1996 | Mitchell |
| 5,503,765 A | 4/1996 | Schepers |
| 5,505,740 A | 4/1996 | Kong |
| 5,545,374 A | 8/1996 | French |
| 5,565,231 A | 10/1996 | Malone |
| 5,576,282 A | 11/1996 | Miracle |
| 5,589,507 A | 12/1996 | Hall, II |
| 5,595,967 A | 1/1997 | Miracle |
| 5,599,781 A | 2/1997 | Haeggberg |
| 5,624,634 A | 4/1997 | Brougham |
| 5,632,676 A | 5/1997 | Kurschner |
| 5,635,195 A | 6/1997 | Hall, II |
| 5,637,755 A | 6/1997 | Nagumo |
| 5,647,997 A | 7/1997 | Holzhauer |
| 5,681,805 A | 10/1997 | Scheuing |
| 5,716,923 A | 2/1998 | MacBeath |
| 5,718,910 A | 2/1998 | Oakes |
| 5,767,308 A | 6/1998 | Thiele |
| 5,780,064 A | 7/1998 | Meisters |
| 5,785,867 A | 7/1998 | Lazonby |
| 5,827,447 A | 10/1998 | Tamura |
| 5,827,808 A | 10/1998 | Appleby |
| 5,841,343 A | 11/1998 | Hapke |
| 5,880,083 A | 3/1999 | Beaujean |
| 5,914,303 A | 6/1999 | Sankey |
| 5,929,012 A | 7/1999 | Del Duca |
| 5,965,033 A | 10/1999 | Huss |
| 5,965,785 A | 10/1999 | Braden |
| 5,977,403 A | 11/1999 | Byers |
| 5,998,350 A | 12/1999 | Burns |
| 6,010,729 A | 1/2000 | Gutzmann |
| 6,022,381 A | 2/2000 | Dias |
| 6,049,002 A | 4/2000 | Mattila |
| 6,103,286 A | 8/2000 | Gutzmann |
| 6,110,883 A | 8/2000 | Petri |
| 6,156,156 A | 12/2000 | Rousu |
| 6,177,393 B1 | 1/2001 | McGregor |
| 6,183,763 B1 | 2/2001 | Beerse |
| 6,207,632 B1 | 3/2001 | Brooker |
| 6,211,237 B1 | 4/2001 | Huss |
| 6,221,341 B1 | 4/2001 | Montgomery |
| 6,238,685 B1 | 5/2001 | Hei |
| 6,274,542 B1 | 8/2001 | Carr |
| 6,284,793 B1 | 9/2001 | Fuchs |
| 6,294,186 B1 | 9/2001 | Beerse |
| 6,326,032 B1 | 12/2001 | Richter |
| 6,399,564 B1 | 6/2002 | Speed |
| 6,407,052 B2 | 6/2002 | Gassenmeier |
| 6,417,151 B1 | 7/2002 | Grothus |
| 6,432,661 B1 | 8/2002 | Heitfeld |
| 6,436,885 B2 | 8/2002 | Biedermann |
| 6,465,483 B1 | 10/2002 | Walter |
| 6,545,047 B2 | 4/2003 | Gutzmann |
| 6,566,318 B2 | 5/2003 | Perkins |
| 6,569,286 B1 | 5/2003 | Withenshaw |
| 6,589,565 B1 | 7/2003 | Richter |
| 6,599,871 B2 | 7/2003 | Smith |
| 6,602,845 B2 | 8/2003 | Stedman |
| 6,627,657 B1 | 9/2003 | Hilgren |
| 6,635,286 B2 | 10/2003 | Hei |
| 6,649,140 B2 | 11/2003 | Paparatto |
| 6,660,289 B1 | 12/2003 | Wilmotte et al. |
| 6,686,324 B2 | 2/2004 | Ramirez |
| 6,689,732 B1 | 2/2004 | Guedira |
| 6,696,093 B2 | 2/2004 | Ney |
| 6,770,774 B2 | 8/2004 | Van De Bovenkamp-Bouwman |
| 6,806,246 B2 | 10/2004 | Preissner |
| 6,866,749 B2 | 3/2005 | Delmas |
| 6,878,680 B2 | 4/2005 | Kitko |
| 6,919,304 B2 | 7/2005 | Dykstra |
| 6,992,225 B2 | 1/2006 | Grimaldi |
| 7,012,154 B2 | 3/2006 | Vineyard |
| 7,060,136 B1 | 6/2006 | Zeiher |
| 7,078,373 B2 | 7/2006 | Burrows |
| 7,148,351 B2 | 12/2006 | Morris |
| 7,169,236 B2 | 1/2007 | Zeiher |
| 7,189,385 B2 | 3/2007 | Montgomery |
| 7,217,295 B2 | 5/2007 | Samain |
| 7,243,664 B2 | 7/2007 | Berger |
| 7,431,775 B2 | 10/2008 | Wang |
| 7,448,255 B2 | 11/2008 | Hoots |
| 7,498,051 B2 | 3/2009 | Man |
| 7,541,324 B2 | 6/2009 | Reinhardt |
| 7,569,232 B2 | 8/2009 | Man |
| 7,569,528 B2 | 8/2009 | Lant |
| 7,598,218 B2 | 10/2009 | Stolte |
| 7,601,789 B2 | 10/2009 | Morris |
| 7,618,545 B2 | 11/2009 | Wakao |
| 7,686,892 B2 | 3/2010 | Smets |
| 7,723,083 B2 | 5/2010 | DiCosimo |
| 7,771,737 B2 | 8/2010 | Man |
| 7,863,234 B2 | 1/2011 | Maki |
| 7,875,720 B2 | 1/2011 | Morris |
| 7,887,641 B2 | 2/2011 | Man |
| 7,910,371 B2 | 3/2011 | Johnson |
| 7,915,445 B2 | 3/2011 | Maatta |
| 7,919,122 B2 | 4/2011 | Okano |
| 7,922,828 B2 | 4/2011 | Smith |
| 7,949,432 B2 | 5/2011 | Rice |
| 7,981,679 B2 | 7/2011 | Rice |
| 7,985,318 B2 | 7/2011 | Shevchenko |
| 8,017,409 B2 | 9/2011 | Tokhtuev |
| 8,030,351 B2 | 10/2011 | Gutzmann |
| 8,071,528 B2 | 12/2011 | Smith |
| 8,080,404 B1 | 12/2011 | Turetsky |
| 8,084,756 B2 | 12/2011 | Tokhtuev |
| 8,110,603 B2 | 2/2012 | Kawabata |
| 8,119,412 B2 | 2/2012 | Kraus |
| 8,153,573 B2 | 4/2012 | Miralles |
| 8,178,336 B2 | 5/2012 | Derkx |

(56) References Cited

U.S. PATENT DOCUMENTS

| | | |
|---|---|---|
| 8,226,939 B2 | 7/2012 | Herdt |
| 8,231,917 B2 | 7/2012 | Herdt |
| 8,236,573 B2 | 8/2012 | Tokhtuev |
| 8,241,624 B2 | 8/2012 | Herdt |
| 8,309,507 B2 | 11/2012 | Fernandez Prieto |
| 8,822,719 B1 | 9/2014 | Li |
| 8,828,910 B2 | 9/2014 | Aksela |
| 9,288,992 B2 | 3/2016 | Li |
| 9,321,664 B2 | 4/2016 | Li |
| 9,518,013 B2 | 12/2016 | Li |
| 9,585,397 B2 | 3/2017 | Li |
| 9,675,076 B2 | 6/2017 | Li |
| 9,902,627 B2 | 2/2018 | Li |
| 10,031,081 B2 | 7/2018 | Li |
| 10,107,756 B2 | 10/2018 | Bolduc |
| 10,165,774 B2 | 1/2019 | Li |
| 11,180,385 B2 | 11/2021 | Li |
| 2002/0041473 A1 | 4/2002 | Hoshiya |
| 2002/0055043 A1 | 5/2002 | Morikawa |
| 2002/0064565 A1 | 5/2002 | Karagoezian |
| 2002/0157189 A1 | 10/2002 | Wang |
| 2002/0188026 A1 | 12/2002 | Singh |
| 2003/0100469 A1 | 5/2003 | Connor |
| 2003/0235623 A1 | 12/2003 | Van Oosterom |
| 2004/0002616 A1 | 1/2004 | Preto |
| 2004/0033269 A1 | 2/2004 | Hei |
| 2004/0035537 A1 | 2/2004 | Delmas |
| 2005/0000908 A1 | 1/2005 | Karlsson |
| 2005/0008526 A1 | 1/2005 | Bianchetti |
| 2005/0226800 A1 | 10/2005 | Wang |
| 2005/0281773 A1 | 12/2005 | Wieland |
| 2006/0040847 A1 | 2/2006 | Weibel |
| 2006/0088498 A1 | 4/2006 | Martin |
| 2006/0173209 A1 | 8/2006 | Vineyard |
| 2006/0199742 A1 | 9/2006 | Arisz |
| 2006/0254001 A1 | 11/2006 | Hoeffkes |
| 2006/0257964 A1 | 11/2006 | Larose |
| 2006/0276366 A1 | 12/2006 | Deljosevic |
| 2007/0042924 A1 | 2/2007 | DiCosimo |
| 2007/0087954 A1 | 4/2007 | Wang |
| 2007/0113875 A1 | 5/2007 | Wang |
| 2007/0163779 A1 | 7/2007 | Rae |
| 2007/0173430 A1 | 7/2007 | Souter |
| 2007/0281002 A1 | 12/2007 | Morales |
| 2008/0095861 A1 | 4/2008 | Walker |
| 2008/0176784 A1 | 7/2008 | Clowes |
| 2008/0312107 A1 | 12/2008 | Harris |
| 2009/0011971 A1 | 1/2009 | Evers |
| 2009/0018049 A1 | 1/2009 | Stolte |
| 2009/0047176 A1 | 2/2009 | Cregger |
| 2009/0061017 A1 | 3/2009 | Pedersen |
| 2009/0088347 A1 | 4/2009 | Mukhopadhyay |
| 2009/0148686 A1 | 6/2009 | Urankar |
| 2009/0175956 A1 | 7/2009 | Buschmann |
| 2009/0221704 A1 | 9/2009 | Aksela |
| 2009/0249557 A1 | 10/2009 | Maki |
| 2009/0269324 A1 | 10/2009 | Herdt |
| 2009/0294382 A1 | 12/2009 | Fukuyo |
| 2010/0021557 A1 | 1/2010 | Li |
| 2010/0021558 A1 | 1/2010 | Dada |
| 2010/0048730 A1 | 2/2010 | Li |
| 2010/0084603 A1 | 4/2010 | Narayan |
| 2010/0108566 A1 | 5/2010 | Scattergood |
| 2010/0140186 A1 | 6/2010 | Huang |
| 2010/0160449 A1 | 6/2010 | Rovison, Jr. |
| 2010/0222242 A1 | 9/2010 | Huang |
| 2010/0227000 A1 | 9/2010 | Ames |
| 2010/0286017 A1 | 11/2010 | Righetto |
| 2010/0308260 A1 | 12/2010 | Maki |
| 2011/0168567 A1 | 7/2011 | Smith |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher, Jr. |
| 2011/0217761 A1 | 9/2011 | Hilgren |
| 2011/0240510 A1 | 10/2011 | De Poortere |
| 2011/0257060 A1 | 10/2011 | Dykstra |
| 2012/0012307 A1 | 1/2012 | Nevin |
| 2012/0024525 A1 | 2/2012 | Svarczkopf |
| 2012/0052134 A1 | 3/2012 | Li |
| 2012/0070339 A1 | 3/2012 | Lawal |
| 2012/0085236 A1 | 4/2012 | McCorriston |
| 2012/0085931 A1 | 4/2012 | Burns |
| 2012/0097614 A1 | 4/2012 | Silva |
| 2012/0149121 A1 | 6/2012 | Tokhtuev |
| 2012/0172441 A1 | 7/2012 | Li |
| 2012/0225943 A1 | 9/2012 | Gohl |
| 2012/0321510 A1 | 12/2012 | Herdt |
| 2013/0018097 A1 | 1/2013 | Bolduc |
| 2014/0097144 A1 | 4/2014 | Li |
| 2016/0200595 A1 | 7/2016 | Li |
| 2019/0225510 A1 | 7/2019 | Li |

FOREIGN PATENT DOCUMENTS

| | | |
|---|---|---|
| WO | 9413395 A1 | 6/1994 |
| WO | 9413776 A1 | 6/1994 |
| WO | 9418299 A1 | 8/1994 |
| WO | 9424869 A1 | 11/1994 |
| WO | 9429509 A1 | 12/1994 |
| WO | 9502030 A1 | 1/1995 |
| WO | 9521122 A1 | 8/1995 |
| WO | 9521290 A1 | 8/1995 |
| WO | 9528471 A1 | 10/1995 |
| WO | 9528472 A1 | 10/1995 |
| WO | 9533816 A1 | 12/1995 |
| WO | 9614384 A1 | 5/1996 |
| WO | 9616148 A1 | 5/1996 |
| WO | 9743393 A2 | 11/1997 |
| WO | 9803513 A1 | 1/1998 |
| WO | 9811189 A1 | 3/1998 |
| WO | 9811777 A1 | 3/1998 |
| WO | 9818893 A1 | 5/1998 |
| WO | 9931215 A1 | 6/1999 |
| WO | 9932598 A1 | 7/1999 |
| WO | 0042145 A1 | 7/2000 |
| WO | 0070951 A1 | 11/2000 |
| WO | 0076963 A1 | 12/2000 |
| WO | 0078911 A1 | 12/2000 |
| WO | 0100765 A1 | 1/2001 |
| WO | 0119414 A1 | 3/2001 |
| WO | 0144176 A1 | 6/2001 |
| WO | 0170030 A2 | 9/2001 |
| WO | 03005818 A1 | 1/2003 |
| WO | 03006581 A2 | 1/2003 |
| WO | 03050343 A2 | 6/2003 |
| WO | 2004044266 A1 | 5/2004 |
| WO | 2005109981 A1 | 11/2005 |
| WO | 2006016145 A1 | 2/2006 |
| WO | 2006018549 A1 | 2/2006 |
| WO | 2006094232 A1 | 9/2006 |
| WO | 2006131503 A2 | 12/2006 |
| WO | 2007013324 A1 | 2/2007 |
| WO | 2008005058 A1 | 1/2008 |
| WO | 2009023492 A2 | 2/2009 |
| WO | 2009040769 A1 | 4/2009 |
| WO | 2009071664 A1 | 6/2009 |
| WO | 2009141548 A2 | 11/2009 |
| WO | 2010050634 A1 | 5/2010 |
| WO | 2010080274 A2 | 7/2010 |
| WO | 2010090125 A1 | 8/2010 |
| WO | 2014055900 A1 | 4/2014 |
| WO | 2014137605 A1 | 9/2014 |

OTHER PUBLICATIONS

Ogata et al.(Biosci. Biotechnol. Biochem., 2002, 66 No. 3, 641-5) (Year: 2002) 2002.

HYDROGEN PEROXIDE AND PERACID STABILIZATION WITH MOLECULES BASED ON A PYRIDINE CARBOXYLIC ACID

CROSS-REFERENCE TO RELATED APPLICATIONS

This application is a Continuation Application of U.S. Ser. No. 16/548,356, filed on Aug. 22, 2019, which, claims priority under 35 U.S.C. § 119 to provisional application Ser. No. 62/721,162, filed Aug. 22, 2018, herein incorporated by reference in its entirety.

FIELD OF THE INVENTION

The present invention relates generally to stable peroxycarboxylic acid compositions comprising a peroxycarboxylic acid, carboxylic acid, hydrogen peroxide and at least one pyridine carboxylic acid stabilizing agent. The stabilizing agents include one or more of 3-pyridinecarboxylic acid, 4-pyridinecarboxylic acid, 5-pyridinecarboxylic acid, 3,4-pyridinedicarboxylic acid, 3,5-pyridinedicarboxylic acid, 4,5-pyridinedicarboxylic acid, 3,4,5-pyridinetricarboxylic acid, oxides thereof, and/or salts thereof. The stable peroxycarboxylic acid compositions are particularly suitable for use in sanitizing equipment to reduce yeasts, spores, bacteria and other contaminants in systems and on surfaces, including those having contact with food, food products and/or components thereof, which require or benefit from infection control suitable for direct contact with such food sources.

BACKGROUND INFORMATION

Peroxycarboxylic acid compositions are increasingly used as biocides in various fields owing to their broad biocidal efficacy and excellent environmental profiles. The most commonly used peroxycarboxylic acid is peracetic acid. Peracetic acid is a colorless, freely water-soluble liquid which has great biocidal efficacy toward various microorganisms, such as bacteria, virus, yeast, fungi and spores. When decomposed, peracetic acid results in acetic acid (vinegar), water and oxygen. Pure peroxycarboxylic acids, such as peracetic acid, however, are unstable and explosive, and thus commercially available peroxycarboxylic acids are usually sold in an equilibrium solution. In addition to the peroxycarboxylic acid, an equilibrium solution also contains the corresponding carboxylic acid, hydrogen peroxide and water. Compared to the peroxycarboxylic acid, hydrogen peroxide only has negligible biocidal efficacy, but may pose environmental issues in some applications if it exceeds the specific release limitation. Furthermore, it has been disclosed that the presence of hydrogen peroxide has negative impacts on the efficacy of peroxycarboxylic acid toward some microorganisms.

Various stabilizers are used in peroxycarboxylic acid compositions to stabilize the compositions. For example, pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts, are used. When used individually at the right level, these stabilizers can significantly improve the stability of the peroxycarboxylic acid compositions, and for the conventional peroxycarboxylic acid compositions, the stability profile achieved with these stabilizers allows for the commercial use of these compositions. Other stabilizers are known for peroxide systems as well.

However, there remain disadvantages to use of many of these stabilizers and the performance of peroxide stabilizers does not perform equally for peroxycarboxylic acid compositions. For example, for peroxycarboxylic acid compositions with high ratios of peroxycarboxylic acid to hydrogen peroxide, the extra stability challenge cannot be met by these stabilizers used in the traditional matter. In a solution of peroxycarboxylic acid, particularly in an aqueous solution thereof, the decomposition of the peroxycarboxylic acid is catalyzed by transitional metal ions. The decomposition of the peroxycarboxylic acid will generate hydroxyl radicals, which will react with peroxycarboxylic acid, leading to further decomposition of peroxycarboxylic acid. Traditionally, metal ion chelating agents such as pyridine-2,6-dicarboxylic acid and HEDP were added to stabilize peroxycarboxylic acid by deactivating the catalytic activity of metal ions. Here, it was surprisingly found that peroxycarboxylic acid could be stabilized by adding selected hydroxy radical scavengers, and these hydroxy radical scavengers do not have the metal ion chelating properties of metal ion chelating agents such as pyridine-2,6-dicarboxylic acid and HEDP. These findings make it possible to identify peroxycarboxylic acid stabilizers that are less toxic, and preferably are known food ingredients.

In addition, the use of chemicals including stabilizers used in peracid compositions for food manufacturers—both direct and indirect food contact—are very strict with requirements for sanitizing compositions that are safe for food contact. Still further, phosphonic acids including HEDP exhibit limited stabilizing capability to peroxycarboxylic acid, thereby presenting challenges in stabilizing peroxycarboxylic acid compositions in warmer climates with elevated ambient temperatures. Further, the U.S. Food and Drug Administration (FDA) has narrow limitations on the quantity of HEDP permitted in food and plant products for animal or human consumption, making it difficult to utilize an effective amount of HEDP as a sole stabilizing agent in compositions that are safe for food contact. See, for example, 21 C.F.R. § 173.370.

There is an ongoing need for stabilizing agents that are both safe and efficacious for direct and indirect food contact and applications on plant products for consumption, such as stabilizing agents that are generally recognized as safe (GRAS). Stabilizing agents such as pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts, have not been classified as a food ingredient, therefore rendering limitations on the amount of these stabilizing agents that can be used on food or plant products for human or animal consumption.

GRAS components are classified by the U.S. Food and Drug Administration as safe for direct human food consumption or as an ingredient based upon current good manufacturing practice conditions of use, as defined for example in 21 C.F.R. Chapter 1, § 170.38 and/or 570.38. Under 21 CFR § 170.30(b), general recognition of safety through scientific procedures requires the same quantity and quality of scientific evidence as is required to obtain approval of the substance as a food additive and ordinarily is based upon published studies, which may be corroborated by unpublished studies and other data and information. U.S.

EPA exemptions for active and inert ingredients in contact with food are codified at 40 C.F.R. Chapter 180 and requires that the amounts indicated are safe for human consumption. Therefore, there remains a need for peroxycarboxylic acid stabilizing agents that are considered GRAS or food additive.

Accordingly, it is an objective to develop stabilized peroxycarboxylic acid compositions safe and efficacious for applications having direct food contact.

It is a further objective to develop stabilized peroxycarboxylic acid compositions that are free of phosphonic acids, such as HEDP, or that reduce the amount of HEDP included in the composition to maintain a sanitizing composition that is safe and efficacious for applications having direct food contact.

It is another objective to develop stabilized peroxycarboxylic acid compositions that only contain components that are GRAS or food additive.

Other objects, advantages and features of the present invention will become apparent from the following specification taken in conjunction with the accompanying drawings.

SUMMARY OF THE INVENTION

An advantage of the invention is to provide stable peroxycarboxylic acid compositions and uses thereof. It is an advantage of the present invention that stable peroxycarboxylic acid compositions are suitable for contacting food surfaces, food processing surfaces, or those involved in the manufacture of food sources while effectively cleaning and/or sanitizing without requiring a rinse step to remove chemicals used in the cleaning and/or sanitizing.

It is an additional advantage of the present invention that the stable peroxycarboxylic acid compositions are biodegradable, decompose into non-hazardous products which therefore leave no toxic traces on the treated surfaces. This is due to the rapid degradation into water, carbon dioxide and organic acid which are recognized as GRAS, as well as the use of stabilizing agents that are approved as GRAS for direct food contact, and therefore do not negatively interfere with the treated surfaces.

In an embodiment, compositions include stabilized peroxycarboxylic acid compositions comprising: a $C_1$-$C_{22}$ carboxylic acid; a $C_1$-$C_{22}$ peroxycarboxylic acid; hydrogen peroxide; and a pyridine carboxylic acid stabilizing agent having the following structure:

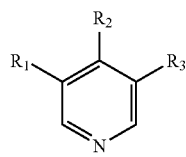

wherein $R_1$, $R_2$ and $R_3$ are independently COOH or H, or a salt thereof. In a further aspect, the pyridine carboxylic acid is a pyridine carboxylic acid oxide having the following structure:

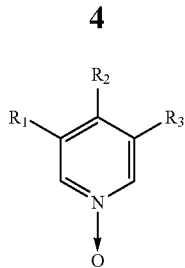

wherein $R_1$, $R_2$ and $R_3$ are independently COOH or H, or a salt thereof. In still further embodiments, the compositions can further include an additional stabilizing agent.

Pyridine carboxylic acid stabilizing agents, such as 3-pyridine carboxylic acid (niacin, nicotinic acid, vitamin B3), presents an advantage over conventional stabilizing agents used to stabilize peroxycarboxylic acid compositions as they are considered GRAS. 3-pyridinecarboxylic acid can be used in food with no limitation other than current good manufacturing practices, affirming the ingredient as GRAS as a direct human food ingredient. Such GRAS classification does not pertain to all pyridine carboxylic acids. Therefore, the use of the stabilizing agents disclosed in the present application can reduce the amount of required stabilizing agents that are not GRAS within the peroxycarboxylic acid composition.

In yet another embodiment, methods for treating a target with the compositions includes, contacting a target with the above composition in a diluted level to form a treated target composition, wherein the treated target composition comprises from about 1 ppm to about 10,000 ppm of the peroxycarboxylic acid, and the contacting step lasts for sufficient time to stabilize or reduce microbial population in and/or on the target or the treated target composition.

In some embodiments, the surface is a food processing surface, food surface, or food product. In other embodiments, the stable peroxycarboxylic acid composition is a direct or indirect contact sanitizer for a food item or a plant item and/or at least a portion of a medium, a container, an equipment, a system or a facility for growing, holding, processing, packaging, storing, transporting, preparing, cooking or serving the food item or the plant item.

In other embodiments, the disclosed compositions are free of any material that is not considered to be GRAS or a food additive ingredient as required for food contact and/or indirect food contact. In further embodiments, the disclosed compositions are food grade acceptable.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
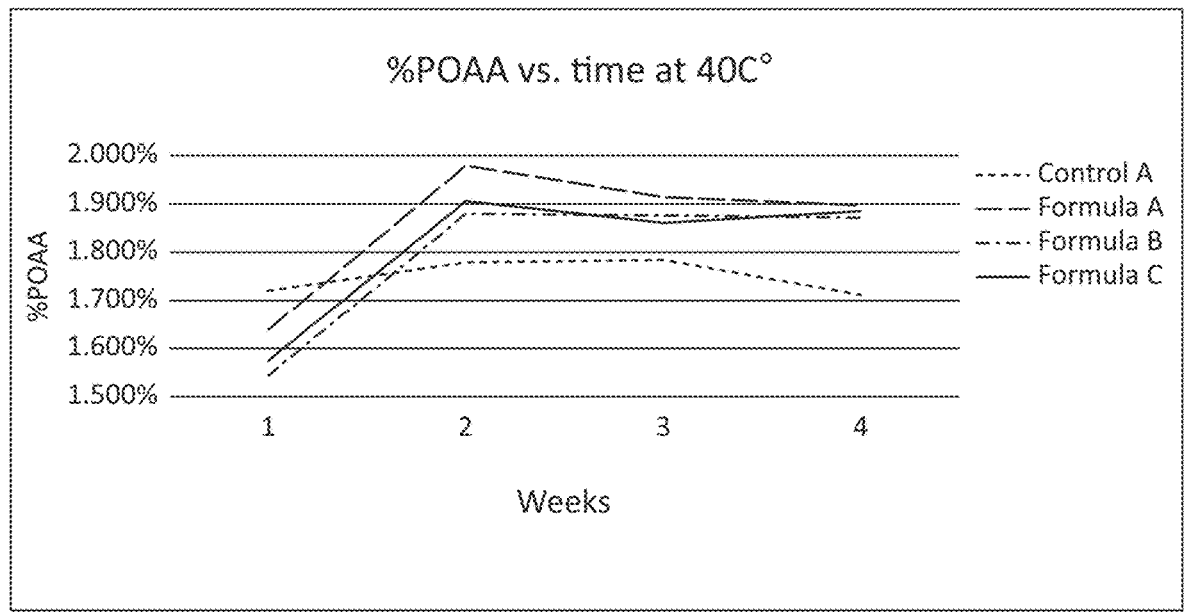
FIG. 1 shows stability of peroxyacetic acid compositions evaluated with various stabilizers.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF INVENTION

The present invention relates to stabilized peroxycarboxylic acid compositions. The compositions have advantages over non-stabilized peroxycarboxylic acids including shelf-stability and transport stability. The embodiments of this invention are not limited to particular compositions, methods of stabilizing and methods of use which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural references unless the context clearly indicates otherwise. Further, all units, prefixes, and symbols may be denoted in their SI accepted form. Numeric ranges recited within the specification are inclusive of the numbers defining the range and include each integer within the defined range.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation; the preferred materials and methods are described herein. In describing and claiming the embodiments of the present invention, the headings provided are not limitations on the embodiments of the invention and the following terminology will be used in accordance with the definitions set out below.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "cleaning," as used herein, means to perform or aid in soil removal, bleaching, microbial population reduction, or combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, "consisting essentially of" means that the methods and compositions may include additional steps, components, ingredients or the like, but only if the additional steps, components and/or ingredients do not materially alter the basic and novel characteristics of the claimed methods and compositions.

As used herein, the term "disinfectant" refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the term "free," "no," "substantially no" or "substantially free" refers to a composition, mixture, or ingredient that does not contain a particular compound or to which a particular compound or a particular compound-containing compound has not been added. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the phrase "food processing surface" or "food surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food antispoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, auto dish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw. Food products include many animal feeds.

The term "generally recognized as safe" or "GRAS," as used herein refers to components classified by the Food and Drug Administration as safe for direct human food consumption or as an ingredient based upon current good manufacturing practice conditions of use, as defined for example in 21 C.F.R. Chapter 1, § 170.38 and/or 570.38. Under 21 CFR § 170.30(b), general recognition of safety through scientific procedures requires the same quantity and quality of scientific evidence as is required to obtain approval of the substance as a food additive and ordinarily is based upon published studies, which may be corroborated by unpublished studies and other data and information. U.S. EPA exemptions for active and inert ingredients in contact with food are codified at 40 C.F. R. Chapter 180 and requires that the amounts indicated are safe for human consumption.

The term "hard surface" refers to a solid, substantially non-flexible surface such as a countertop, tile, floor, wall, panel, window, plumbing fixture, kitchen and bathroom furniture, appliance, engine, circuit board, and dish. Hard surfaces may include for example, health care surfaces and food/plant/animal processing surfaces.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

As used herein, the phrase "plant", "plant product", or "plant item" includes any plant substance or plant-derived substance. These plant or plant-derived substances include, but are not limited to, seeds, nuts, nut meats, cut flowers, plants or crops grown or stored in a greenhouse, house plants, and the like. Plant products include many animal feeds.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, the term "water" for treatment according to the invention includes a variety of sources, such as freshwater, pond water, sea water, salt water or brine source, brackish water, recycled water, or the like. Waters are also understood to optionally include both fresh and recycled water sources (e.g. "produced waters"), as well as any combination of waters for treatment according to the invention. In some embodiments, produced water (or reuse water) refers to a mixture of water that comprises both water recycled from previous or concurrent oil- and gas-field operations, e.g., fracking, and water that has not been used in oil- and gas-field operations, e.g., fresh water, pond water, sea water, etc.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

It is understood that aspects and embodiments of the invention described herein include "consisting" and/or "consisting essentially of" aspects and embodiments.

Compositions

According to an embodiment, stable peroxycarboxylic acid compositions are provided and include at least one $C_1$-$C_{22}$ carboxylic acid, at least one $C_1$-$C_{22}$ peroxycarboxylic acid, hydrogen peroxide, at least one pyridine carboxylic acid stabilizing agent, and optionally an additional stabilizing agent. In an aspect, the pyridine carboxylic acid has the following structure:

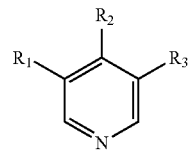

wherein $R_1$, $R_2$ and $R_3$ are independently COOH or H, or a salt thereof. In a further aspect, the pyridine carboxylic acid is a pyridine carboxylic acid oxide having the following structure:

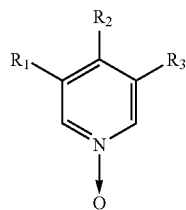

wherein $R_1$, $R_2$ and $R_3$ are independently COOH or H, or a salt thereof.

In an aspect, the compositions include the exemplary ranges shown in Table 1 in weight percentage of the liquid concentrated equilibrium compositions.

TABLE 1

| Material | First Exemplary Range wt-% | Second Exemplary Range wt-% | Third Exemplary Range wt-% |
|---|---|---|---|
| Solvent (e.g. Water) | 1-75 | 10-60 | 20-50 |
| Peroxycarboxylic Acid | 0.1-40 | 1-40 | 1-20 |
| Carboxylic Acid | 0.1-80 | 1-80 | 1-50 |
| Hydrogen Peroxide | 1-90 | 1-80 | 1-50 |
| Pyridine Carboxylic Acid | 0.001-10 | 0.01-5 | 0.1-2 |
| Acid Additive | 0-10 | 0-8 | 0-5 |
| Additional Functional Ingredients | 0-25 | 0-20 | 0-10 |

Without being limited to a particular mechanism of action, the pyridine carboxylic acids provide unexpected stabilization of peracids in comparison to isomer structures of 2,6-pyridine (mono or di) carboxylic acids which are known chelants. The 3-pyridinecarboxylic acid (niacin, nicotinic acid, Vitamin B3), 4-pyridinecarboxylic acid (isonicotinic acid), 5-pyridinecarboxylic acid, 3,4-pyridinedicarboxylic acid, 3,5-pyridinedicarboxylic acid (dinicotinic acid), 4,5-pyridinedicarboxylic acid, 3,4,5-pyridinetricarboxylic acid, oxides thereof, and/or salts thereof are stabilizing agents for the peroxycarboxylic acid compositions and unexpectedly provide distinct bioactive molecules that do not form metal complexes as the carboxylic acid group is not adjacent to the nitrogen atom of the pyridine ring. Conventional stabilizing agents stabilize peracids through the efficient chelating of transitional metal ions. This is a result of the at least one carboxylic acid group adjacent to the nitrogen of the pyridine ring, providing efficacious chelating, ligand and radical scavenger. However, the pyridine carboxylic acid structures according to the stabilized compositions do not provide such a chelating effect due to their structural distinctions. Therefore, it was not expected that the claimed pyridine carboxylic acids would provide stabilizing efficacy for the acidic peroxycarboxylic acid compositions among other activity, both in comparison to conventional stabilizers, including phosphates, phosphonates and/or other metal chelating stabilizers (e.g. HEDP, NTA, DPA).

Without being limited to a particular theory or mechanism of the invention, pyridine carboxylic acids disclosed in the present application, such as nicotinic acid and isonicotinic acid, have high radical-scavenging activity. Therefore, the inclusion of the pyridine carboxylic acids disclosed in the present application effectively quench hydroxyl radicals generated (or different radicals further generated) during the decomposition of the peroxycarboxylic acid, preventing them from attacking the peroxycarboxylic acid, and resulting in stabilization of the peroxycarboxylic acid composition.

The compositions described herein provides peroxycarboxylic acid compositions stabilized and therefore suitable for use under acidic, equilibrium compositions. In some aspects the compositions, whether generated in situ or on site from one or more premix compositions or whether provided in a concentrated equilibrium composition, in a use solution have a pH at about 4 or less. The compositions can also be used to stabilize compositions having high ratios of peroxycarboxylic acids to hydrogen peroxide, wherein the concentration of the peroxyacids greatly exceed the hydrogen peroxide.

Pyridine Carboxylic Acid Compounds

The compositions include at least one pyridine carboxylic acid stabilizing agent. The stabilizing agents can include 3-pyridinecarboxylic acid (niacin, nicotinic acid, Vitamin B3), 4-pyridinecarboxylic acid (isonicotinic acid), 5-pyridinecarboxylic acid, 3,4-pyridinedicarboxylic acid, 3,5-pyridinedicarboxylic acid (dinicotinic acid), 4,5-pyridinedicarboxylic acid, 3,4,5-pyridinetricarboxylic acid, oxides thereof, and/or salts thereof. Beneficially, the pyridine carboxylic acid stabilizing agents prevent the decomposition of the peroxycarboxylic acid in an equilibrium composition. In addition, pyridine carboxylic acid stabilizing agents prevent an equilibrium peracid composition from reaching their self-accelerating decomposition temperatures (SADT). By elevating the SADTs of the compositions the stabilizers contribute significant safety benefits for transportation and storage of the compositions. In some aspects, the stabilizing agents prevent the composition from exceeding SADT limitation of the peroxycarboxylic acid compositions.

The pyridine carboxylic acids can have the following structure:

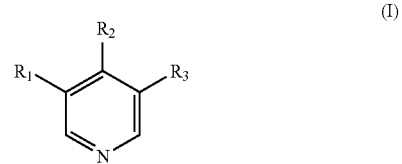

(I)

wherein $R_1$, $R_2$ and $R_3$ are independently COOH or H, or a salt thereof. Exemplary structures include the following:

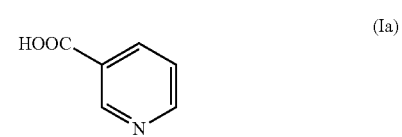

(Ia)

(Ib)

-continued

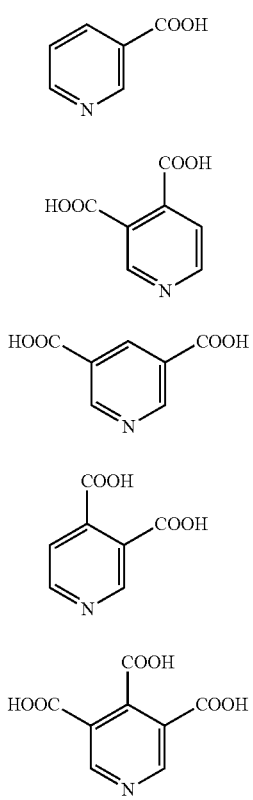

In a further aspect, the pyridine carboxylic acids can include pyridine carboxylic acid oxides having the following structure:

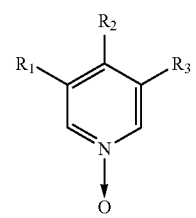
(II)

wherein $R_1$, $R_2$ and $R_3$ are independently COOH or H, or a salt thereof. Exemplary structures include the following:

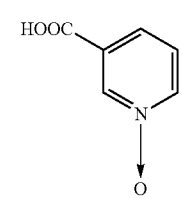
(IIa)

-continued

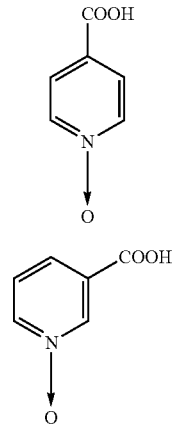

The pyridine carboxylic acid stabilizer can be used at any suitable concentration. In some embodiments, a concentrated equilibrium composition has a concentration of the pyridine carboxylic acid stabilizer from about 0.001 wt-% to about 10 wt-%, or from about 0.005 wt-% to about 10 wt-%. In still other embodiments, the pyridine carboxylic acid stabilizer has a concentration from about 0.01 wt-% to about 5 wt-%, from about 0.05 wt-% to about 5 wt-%, from about 0.1 wt-% to about 2 wt-%, or more preferably from about 0.5 wt-% to about 2 wt-%. Without limiting the scope of invention, the numeric ranges are inclusive of the numbers defining the range and include each integer within the defined range.

Peracids

According to the invention, a peroxycarboxylic acid (i.e. peracid) is included for antimicrobial efficacy in the sanitizing compositions disclosed herein. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid" and "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in, for example, U.S. Pat. Nos. 8,344,026, 8,809,392 and 9,359,295, each of which are incorporated herein by reference in their entirety. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)n in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Preferably, a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like.

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like. Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

According to the invention, alkyl, alkenyl, alicyclic groups, and heterocyclic groups can be unsubstituted or substituted by, for example, aryl, heteroaryl, C1-4 alkyl, C1-4 alkenyl, C1-4 alkoxy, amino, carboxy, halo, nitro, cyano, —SO3H, phosphono, or hydroxy. When alkyl, alkenyl, alicyclic group, or heterocyclic group is substituted, preferably the substitution is C1-4 alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

According to the invention, aryl and heteroaryl groups can be unsubstituted or substituted on the ring by, for example, aryl, heteroaryl, alkyl, alkenyl, alkoxy, amino, carboxy, halo, nitro, cyano, —SO3H, phosphono, or hydroxy. When aryl, aralkyl, or heteroaryl is substituted, preferably the substitution is C1-4 alkyl, halo, nitro, amido, hydroxy, carboxy, sulpho, or phosphono. In one embodiment, R includes aryl substituted with C1-4 alkyl.

Peracids suitable for use include any peroxycarboxylic acids, including varying lengths of peroxycarboxylic acids (e.g. C1-22) that can be prepared from the acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid anhydride, carboxylic acid anhydride, sodium alcoholate or alkyl and aryl esters. Alternatively, peracids can be prepared through non-equilibrium reactions, which may be generated for use in situ, such as the methods disclosed in U.S. Pat. Nos. 8,846,107 and 8,877,254, which are incorporated herein by reference in their entirety. Preferably a composition of the invention includes peroxyformic acid, peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyacetic acid. In another embodiment, a peroxycarboxylic acid has R that is an alkyl of 1-22 carbon atoms substituted with a hydroxyl group or other polar substituent such that the substituent improves the water solubility. Methods of preparing peroxyacetic acid are known to those of skill in the art including those disclosed in U.S. Pat. No. 2,833,813, which is herein incorporated herein by reference in its entirety.

In another embodiment, a sulfoperoxycarboxylic acid has the following structure:

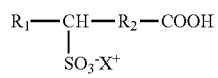

wherein R1 is hydrogen, or a substituted or unsubstituted alkyl group; R2 is a substituted or unsubstituted alkylene group; X is hydrogen, a cationic group, or an ester forming moiety; or salts or esters thereof. In some embodiments, R1 is a substituted or unsubstituted Cm alkyl group; X is hydrogen a cationic group, or an ester forming moiety; R2 is a substituted or unsubstituted Cn alkyl group; m=1 to 10; n=1 to 10; and m+n is less than 18, or salts, esters or mixtures thereof.

In some embodiments, R1 is hydrogen. In other embodiments, R1 is a substituted or unsubstituted alkyl group. In some embodiments, R1 is a substituted or unsubstituted alkyl group that does not include a cyclic alkyl group. In some embodiments, R1 is a substituted alkyl group. In some embodiments, R1 is an unsubstituted C1-C9 alkyl group. In some embodiments, R1 is an unsubstituted C7 or C8 alkyl. In other embodiments, R1 is a substituted C8-C10 alkylene group. In some embodiments, R1 is a substituted C8-C10 alkyl group is substituted with at least 1, or at least 2 hydroxyl groups. In still yet other embodiments, R1 is a substituted C1-C9 alkyl group. In some embodiments, R1 is a substituted C1-C9 substituted alkyl group is substituted with at least 1 SO3H group. In other embodiments, R1 is a C9-C10 substituted alkyl group. In some embodiments, R1 is a substituted C9-C10 alkyl group wherein at least two of the carbons on the carbon backbone form a heterocyclic group. In some embodiments, the heterocyclic group is an epoxide group.

In some embodiments, R2 is a substituted C1-C10 alkylene group. In some embodiments, R2 is a substituted C8-C10 alkylene. In some embodiments, R2 is an unsubstituted C6-C9 alkylene. In other embodiments, R2 is a C8-C10 alkylene group substituted with at least one hydroxyl group. In some embodiments, R2 is a C10 alkylene group substituted with at least two hydroxyl groups. In other embodiments, R2 is a C8 alkylene group substituted with at least one SO3H group. In some embodiments, R2 is a substituted C9 group, wherein at least two of the carbons on the carbon backbone form a heterocyclic group. In some embodiments, the heterocyclic group is an epoxide group. In some embodiments, R1 is a C8-C9 substituted or unsubstituted alkyl, and R2 is a C7-C8 substituted or unsubstituted alkylene.

In additional embodiments a sulfoperoxycarboxylic acid is combined with a single or mixed peroxycarboxylic acid composition, such as a sulfoperoxycarboxylic acid with peroxyacetic acid and peroxyoctanoic acid (PSOA/POAA/ POAA). In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyacetic acid and peroxyoctanoic acid, such as disclosed in U.S. Pat. No. 5,314,687 which is herein incorporated by reference in its entirety. In an aspect, the peracid mixture is a hydrophilic peracetic acid and a hydrophobic peroctanoic acid, providing antimicrobial synergy. In an aspect, the synergy of a mixed peracid system allows the use of lower dosages of the peracids.

In another embodiment, a tertiary peracid mixture composition, such as peroxysulfonated oleic acid, peracetic acid and peroctanoic acid are employed, such as disclosed in U.S. Pat. No. 8,344,026 which is incorporated herein by reference in its entirety. Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Various commercial formulations of peracids are available, including for example peracetic acid (approximately 15%) available as EnviroSan (Ecolab, Inc., St. Paul MN). Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

In an aspect, any suitable C1-C22 percarboxylic acid can be used in the present compositions. In some embodiments, the C1-C22 percarboxylic acid is a C2-C20 percarboxylic acid. In other embodiments, the C1-C22 percarboxylic is a C1, C2, C3, C4, C5, C6, C7, C8, C9, C10, C11, C12, C13, C14, C15, C16, C17, C18, C19, C20, C21, or C22 carboxylic acid. In still other embodiments, the C1-C22 percarboxylic acid comprises peroxyacetic acid, peroxyoctanoic acid and/or peroxysulfonated oleic acid.

In an aspect of the invention, a peracid may be selected from a concentrated composition having a ratio of hydrogen peroxide to peracid from about 0:10 to about 10:0, preferably from about 0.5:10 to about 10:0.5, preferably from about 1:8 to 8:1. Various concentrated peracid compositions having the hydrogen peroxide to peracid ratios of about 0.5:10 to about 10:0.5, preferably from about 1:8 to 8:1, may be employed to produce a use solution for treatment according to the methods of the invention. In a further aspect of the invention, a peracid may have a ratio of hydrogen peroxide to peracid as low as from about 0.01 part hydrogen peroxide to about 1 part peracid. Without limiting the scope of invention, the numeric ranges are inclusive of the numbers defining the range and include each integer within the defined range.

Obtaining the preferred hydrogen peroxide to peroxycarboxylic acid ratios in a peracid composition may be obtained by a variety of methods suitable for producing a very low hydrogen peroxide to peracid ratio. In an aspect, equilibrium peracid compositions may be distilled to recover a very low hydrogen peroxide peracid mixture. In yet another aspect, catalysts for hydrogen peroxide decomposition may be combined with a peracid composition, including for example, peroxide-reducing agents and/or other biomimetic complexes. In yet another aspect, perhydrolysis of peracid precursors, such as esters and amides may be employed to obtain peracids with very low hydrogen peroxide.

In a preferred aspect, the C1-C22 percarboxylic acid can be used at any suitable concentration. In some embodiments, the C1-C22 percarboxylic acid has a concentration from about 0.1 wt-% to about 40 wt-% in a concentrated equilibrium composition. In other embodiments, the C1-C22 percarboxylic acid has a concentration from about 1 wt-% to about 40 wt-%, or from about 1 wt-% to about 20 wt-%. In still other embodiments, the C1-C22 percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%. Without limiting the scope of invention, the numeric ranges are inclusive of the numbers defining the range and include each integer within the defined range.

Carboxylic Acid

The present invention includes a carboxylic acid with the peracid composition and hydrogen peroxide. A carboxylic acid includes any compound of the formula R—(COOH)n in which R can be hydrogen, alkyl, alkenyl, alkyne, acylic, alicyclic group, aryl, heteroaryl, or heterocylic group, and n is 1, 2, or 3. Preferably R includes hydrogen, alkyl, or alkenyl. The terms "alkyl," "alkenyl," "alkyne," "acylic," "alicyclic group," "aryl," "heteroaryl," and "heterocyclic group" are as defined above with respect to peracids.

Examples of suitable carboxylic acids according to the equilibrium systems of peracids according to the invention include a variety monocarboxylic acids, dicarboxylic acids, and tricarboxylic acids. Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc. Dicarboxylic acids include, for example, adipic acid, fumaric acid, glutaric acid, maleic acid, succinic acid, malic acid, tartaric acid, etc. Tricarboxylic acids include, for example, citric acid, trimellitic acid, isocitric acid, agaicic acid, etc.

In an aspect of the invention, a particularly well suited carboxylic acid is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. Preferably a composition of the invention includes acetic acid, octanoic acid, or propionic acid, lactic acid, heptanoic acid, octanoic acid, or nonanoic acid. Additional examples of suitable carboxylic acids are employed in sulfoperoxycarboxylic acid or sulfonated peracid systems.

Any suitable C1-C22 carboxylic acid can be used in the present compositions. In some embodiments, the C1-C22 carboxylic acid is a C2-C20 carboxylic acid. In other embodiments, the C1-C22 carboxylic acid is a C1, C2, C3, C4, C5, C6, C7, C8, C9, C10, C11, C12, C13, C14, C15, C16, C17, C18, C19, C20, C21, or C22 carboxylic acid. In still other embodiments, the C1-C22 carboxylic acid comprises acetic acid, octanoic acid and/or sulfonated oleic acid.

The C1-C22 carboxylic acid can be used at any suitable concentration. In some embodiments, the C1-C22 carboxylic acid has a concentration in an equilibrium composition from about 0.1 wt-% to about 80 wt-%. In other embodiments, the C1-C22 carboxylic acid has a concentration from about 1 wt-% to about 80 wt-%. In still other embodiments, the C1-C22 carboxylic acid has a concentration at about 1 wt-% to about 50 wt-%. Without limiting the scope of invention, the numeric ranges are inclusive of the numbers defining the range and include each integer within the defined range.

Hydrogen Peroxide

The present invention includes hydrogen peroxide. Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid. Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and are generally innocuous to incidental contact and are environmentally friendly.

In one aspect of the invention, hydrogen peroxide is initially in an antimicrobial peracid composition in an amount effective for maintaining an equilibrium between a carboxylic acid, hydrogen peroxide, and a peracid. The amount of hydrogen peroxide should not exceed an amount that would adversely affect the antimicrobial activity of a composition of the invention. In further aspects of the invention, hydrogen peroxide concentration can be significantly reduced within an antimicrobial peracid composition. In some aspects, an advantage of minimizing the concentration of hydrogen peroxide is that antimicrobial activity of a composition of the invention is improved as compared to conventional equilibrium peracid compositions.

The hydrogen peroxide can be used at any suitable concentration. In some embodiments, a concentrated equilibrium composition has a concentration of hydrogen peroxide from about 0.5 wt-% to about 90 wt-%, or from about 1 wt-% to about 90 wt-%. In still other embodiments, the hydrogen peroxide has a concentration from about 1 wt-% to about 80 wt-%, from about 1 wt-% to about 50 wt-%. Without limiting the scope of invention, the numeric ranges are inclusive of the numbers defining the range and include each integer within the defined range. Beneficially, the compositions and methods of the invention in providing stabilized equilibrium peracid compositions, are not reliant and/or limited according to any particular ratio of hydrogen peroxide to peracid for such enhanced stability.

In an aspect of the invention, the peroxycarboxylic acid compositions exhibits less than 40% loss of peroxycarboxylic acid and/or hydrogen peroxide at a storage temperature of about 40° C. after 4 weeks, preferably less than 20% loss of peroxycarboxylic acid and/or hydrogen peroxide at a storage temperature of about 40° C. after 4 weeks, and most preferably less than 10% loss of peroxycarboxylic acid and/or hydrogen peroxide at a storage temperature of about 40° C. after 4 weeks.

Acid Additives

In some embodiments, the present composition is a strongly acidic peracid as a result of inclusion of a strong acid. In some aspects the peracid composition has a use solution pH of 4 or less, and preferably has a use solution pH of 3 or less. In some embodiments, the present composition includes an inorganic acid. In preferred embodiments, the present composition includes a mineral acid.

Particularly suitable acids include sulfuric acid ($H_2SO_4$), sodium hydrogen sulfate, nitric acid, sulfamic acid and sulfonic acids both alkyl and aryl, in particular methane sulfonic acid and dodecylbenzene, toluene, xylene, naphthalene and cumene sulfonic acid, and/or phosphoric acid (H3PO4). Additional phosphonic acids which may be used according to the invention include, for example, aminotrimethylene phosphonic acid, ethylene diamin tetramethylene phosphonic acid, hexamethylene diamin tetramethylene phosphonic acid, diethylene triamin tetramethylene phosphonic acid, and 1-hydroxyethylidene-1,1-diphosphonic acid (HEDP).

The acid additives providing the strong acidity of the peracid compositions can be used at any suitable concentration. In some embodiments, a concentrated equilibrium composition has a concentration of the acid from about 0.5 wt-% to about 50 wt-%, or from about 1 wt-% to about 50 wt-%. In still other embodiments, the acid has a concentration from about 1 wt-% to about 20 wt-%, or more preferably from about 5 wt-% to about 20 wt-%. Without limiting the scope of invention, the numeric ranges are inclusive of the numbers defining the range and include each integer within the defined range.

Additional Stabilizing Agents

Although not required for stabilizing the peroxycarboxylic acid compositions, additional stabilizing agents can be included in the compositions. Exemplary disclosure of distinct pyridine carboxylic acid isomers is included in U.S. Pat. No. 9,321,664, which is incorporated herein by reference in its entirety. Exemplary stabilizing agents include dipicolinic acid or 2,6-pyridinedicarboxylic acid (DPA), picolinic acid, or a salt thereof. Dipicolinic acid has been used as a stabilizer for peracid compositions, such as disclosed in WO 91/07375 and U.S. Pat. No. 2,609,391, which are herein incorporated by reference in their entirety. Additional conventional stabilizing agents, e.g. a phosphonate-based stabilizer, can be included in the compositions to beneficially provide further increase in stability of the composition. Exemplary stabilizers include phosphoric acid and salts, pyrophosphoric acid and salts and most commonly 1-hydroxyethylidene-1,1-diphosphonic acid (HEDP) and salts. When additional stabilizing agents are included, the compositions of the present invention beneficially reduce the amount of additional stabilizing agents needed to stabilize the peroxycarboxylic acid composition.

Additional stabilizing agents may be present in amounts sufficient to provide the intended stabilizing benefits, including in amounts from about 0.001 wt-% to about 25 wt-%, 0.01 wt-% to about 10 wt-%, and more preferably from about 0.01 wt-% to about 1 wt-%. Without limiting the scope of invention, the numeric ranges are inclusive of the numbers defining the range and include each integer within the defined range.

In some embodiments, HEDP and salts are included in amounts from about 0.001 wt-% to 7 wt-%, preferably from 0.001 wt-% to 5 wt-%, and more preferably from about 0.01 wt-% to about 1 wt-%. Without limiting the scope of the invention, the numeric ranges are inclusive of the numbers defining the range and include each integer within the defined range.

In further embodiments, the synergy between the pyridine carboxylic acid stabilizing agent and HEDP reduces the amount of HEDP included in the composition to less than 15 ppm in use solution, preferably less than 13 ppm in use solution, and more preferably less than 10 ppm. Without limiting the scope of the invention, the numeric ranges are inclusive of the numbers defining the range and include each integer within the defined range.

Additional Functional Ingredients

In some embodiments, the compositions can further comprise additional functional ingredients. In some embodiments, the acidic peracid compositions including the pyridine carboxylic acid stabilizing agent, peroxycarboxylic acid, carboxylic acid, hydrogen peroxide and water make up a large amount, or even substantially all of the total weight of the peracid compositions. For example, in some embodiments few or no additional functional ingredients are disposed therein.

In other embodiments, mineral acids, additional stabilizing agents and/or additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used. In some aspects, the compositions may include defoaming agents, surfactants, fluorescent tracer molecules, additional antimicrobial agents, enzymes, anti-redeposition agents, bleaching agents, solubility modifiers, viscosity enhancers, dispersants, rinse aids, metal protecting agents, stabilizing agents, corrosion inhibitors, scale inhibitors, fragrances and/or dyes, rheology modifiers or thickeners, hydrotropes or couplers, buffers, solvents and the like.

In preferred embodiments, the compositions further include substances that aid in the solubilization of the stabilizing agent(s), including for example, hydrotropes such as sodium xylene sulfonate (SXS), sodium cumene sulfonates (SCS), surfactants, such as anionic surfactants and nonionic surfactants, and a defoaming agent. In further aspects, the composition may utilize alternative hydrotropes for solubilization of the stabilizing agent, including for example, n-octanesulfonate, a xylene sulfonate, a naphthalene sulfonate, ethylhexyl sulfate, lauryl sulfate, an amine oxide, etc.

In preferred embodiments, the compositions do not include any components which are not GRAS, as required for food contact and/or indirect food contact. In still other embodiments, the compositions do not include any components which impart an unfavorable odor and/or flavor. In still other embodiments, the compositions do not include any essential oils and/or terpenes, or metal ions (i.e. Ag, V, Nb, Ta, W, Co, In, Tl).

The additional functional ingredients can be used at any suitable concentration. In some embodiments, additional functional ingredients have a concentration from about 0 wt-% to about 25 wt-%, or from about 0 wt-% to about 20 wt-%. In still other embodiments, the additional functional ingredients have a concentration from about 0.01 wt-% to about 5 wt-%, from about 0.05 wt-% to about 5 wt-%, from about 0.1 wt-% to about 2 wt-%, or more preferably from about 0.5 wt-% to about 2 wt-%. Without limiting the scope of invention, the numeric ranges are inclusive of the numbers defining the range and include each integer within the defined range.

Methods of Delivery and Methods of Use

The stabilized peroxycarboxylic acid compositions are suitable for storing, transporting and/or applying for treatment a stabilized peroxycarboxylic acid composition. In an embodiment, at least about 80% of the peroxycarboxylic acid activity is retained after storage for any suitable time under any suitable conditions, e.g., retaining at least about 80% of the peroxycarboxylic acid activity after storage of about 30 days at about 40° C. or above. Preferably, the methods include retaining at least about 85%, at least about 90%, or at least about 95% or higher of the peroxycarboxylic acid activity after storage of about 30 days at about 40° C. or above. In still another aspect, the stabilized compositions are used for sanitizing surfaces, targets and/or products. The compositions are particularly suitable for use as a hard surface sanitizer and/or disinfectant, a CIP sanitizer, food and/or tissue treatment sanitizer, an environmental disinfectant, a laundry bleach and disinfectant, and/or an indirect food contact sanitizer. The present methods can be used in the methods, processes or procedures described and/or claimed in U.S. Pat. Nos. 5,200,189, 5,314,687, 5,718,910, 6,165,483, 6,238,685B1, 8,017,409 and 8,236,573, each of which are herein incorporated by reference in their entirety.

The compositions are particularly suitable for direct or indirect contact sanitizer for a food item or a plant item and/or at least a portion of a medium, a container, an equipment, a system or a facility for growing, holding, processing, packaging, storing, transporting, preparing, cooking or serving the food item or the plant item. The present methods can be used for treating any suitable plant item. In some embodiments, the plant item is a grain, fruit, vegetable or flower plant item, a living plant item or a harvested plant item, and/or animal feed. In addition, the present methods can be used for treating any suitable food item, e.g., an animal product, an animal carcass or an egg, a fruit item, a vegetable item, or a grain item. In still other embodiments, the food item may include a fruit, grain and/or vegetable item.

The present methods can be used for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The present methods are particularly well suited for treating and sanitizing equipment, such as fermentation equipment which are vulnerable to yeasts, spores and bacteria in the systems and within a mash source generated. This presents unique challenges requiring antimicrobial and sanitizing methods that come into direct contact with feed sources, namely animal feed. Accordingly, there is a unique benefit of providing the stabilized peroxycarboxylic acid compositions have food-safe pyridine carboxylic acid stabilizers employed therein. In a preferred embodiment, nicotinic acid (Vitamin B, niacin, 3-pyridine carboxylic acid) is food safe for such contact. Beneficially, the stabilized peroxycarboxylic acid compositions can be used to sanitize a surface without the need to rinse the surfaces thereafter.

The present methods can be used to stabilize or reduce a microbial population in and/or on the target or the treated target composition, wherein the target is an animal tissue, or used as a sanitizer and disinfectant on a skin surface, for example teats. The contacting step minimizes or does not induce an organoleptic effect in and/or on the animal tissue and/or products of the same (e.g., milk). Typical organoleptic properties include the aspects of food or other substances as experienced by the senses, including taste, sight, smell, and touch, in cases where dryness and moisture are to be considered.

The present methods can be used for treating a target that is at least a portion of a solid surface or liquid media. In some embodiments, the solid surface is an inanimate solid surface. The inanimate solid surface can be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment, or the surface of a fabric.

The various methods of treatment can include the use of any suitable level of the peroxycarboxylic acid. In some embodiments, the treated target composition comprises from about 1 ppm to about 10,000 ppm, about 10 ppm to about 1,000 ppm, or any ranges therebetween, of the peroxycarboxylic acid, including any of the peroxycarboxylic acid compositions according to the invention.

In still another aspect, the stabilized peroxycarboxylic acid compositions can be used in water treatment methods and other industrial processes uses of the compositions for sanitizing surfaces and/or products. In some aspects, the invention includes methods of using the peroxycarboxylic acid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid compositions are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this invention could be applied are in process water applications (flume water, shower water, washers, thermal processing waters, brewing, fermentation, CIP (clean in place), hard surface sanitization, etc.), Ethanol/Bio-fuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields-oil and gas wells/flow line, water systems, gas systems, etc.), and in particular water systems where the installed process equipment exhibits lowered compatibility to halogenated biocides.

The methods by which the peroxycarboxylic acid compositions are introduced into the aqueous fluids or liquid systems are not critical. Introduction of the peracid compositions may be carried out in a continuous or intermittent manner and will depend on the type of water and/or liquid being treated. In some embodiments, the peracid compositions are introduced into an aqueous fluid according to the methods disclosed in U.S. patent application Ser. No. 13/645,671, titled "New Method and Arrangement for Feeding Chemicals into a Hydrofracturing Process and Oil and Gas Applications", which is hereby incorporated by reference in its entirety.

The various applications of use described herein provide the peroxycarboxylic acid compositions to a surface, liquid and/or product in need of antimicrobial and/or sanitizing treatment. Beneficially, the compositions of the invention are fast-acting. However, the present methods require a certain minimal contact time of the compositions with the surface, liquid and/or product in need of treatment for occurrence of sufficient antimicrobial effect. The contact time can vary with concentration of the use compositions, method of applying the use compositions, temperature of the use compositions, pH of the use compositions, amount of the surface, liquid and/or product to be treated, amount of soil or substrates on/in the surface, liquid and/or product to be treated, or the like. The contact or exposure time can be at least about 15 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. In other embodiments, the exposure time is a few hours to days. The contact time will further vary based upon the concentration of peracid in a use solution.

In some embodiments, the stable peroxycarboxylic acid composition can be applied to a surface by means of spray, wipe, dip or submerging all or part of the surface in the composition.

The present methods can be conducted at any suitable temperature. In some embodiments, the present methods are conducted at a temperature ranging from about 0° C. to about 70° C., e.g., from about 0° C. to about 4° C. or 5° C., from about 5° C. to about 10° C., from about 11° C. to about 20° C., from about 21° C. to about 30° C., from about 31° C. to about 40° C., including at about 37° C., from about 41° C. to about 50° C., from about 51° C. to about 60° C., or from about 61° C. to about 70° C.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms.

The present methods can be used to achieve any suitable reduction of the microbial population in and/or on the target or the treated target composition. In some embodiments, the present methods can be used to reduce the microbial population in and/or on the target or the treated target composition by at least one log 10. In other embodiments, the present methods can be used to reduce the microbial population in and/or on the target or the treated target composition by at least two log 10. In still other embodiments, the present methods can be used to reduce the microbial population in and/or on the target or the treated target composition by at least three log 10.

The present methods achieve less than 40% loss of peroxycarboxylic acid and/or hydrogen peroxide at a storage temperature of about 40° C. after 4 weeks, preferably less than 20% loss of peroxycarboxylic acid and/or hydrogen peroxide at a storage temperature of about 40° C. after 4 weeks, and most preferably less than 10% loss of peroxycarboxylic acid and/or hydrogen peroxide at a storage temperature of about 40° C. after 4 weeks. Further, the present methods maintain peroxycarboxylic acid and/or hydrogen peroxide stability without including any essential oils and/or terpenes, or without forming metal complexes or metal ions.

The peroxycarboxylic acid compositions may include concentrate compositions or may be diluted to form use compositions. In general, a concentrate refers to a composition that is intended to be diluted with water to provide a use solution that contacts a surface, liquid and/or product in need of treatment to provide the desired cleaning, sanitizing or the like. The peroxycarboxylic acid composition that contacts the surface, liquid and/or product in need of treatment can be referred to as a concentrate or a use composition (or use solution) dependent upon the formulation employed in methods according to the invention. It should be understood that the concentration of the peroxycarboxylic acid in the composition will vary depending on whether the composition is provided as a concentrate or as a use solution.

A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications to the embodiments of the invention to adapt it to various usages and conditions.

Example 1

Stability of peroxyacetic acid compositions were evaluated using nicotinic acid in comparison to dipicolinic acid and a negative control without a stabilizing agent. The evaluated peroxyacetic acid compositions are shown in wt-% in Table 2.

TABLE 2

| Raw material | Control A | Formula A | Formula B | Formula C |
|---|---|---|---|---|
| DI water | 42 | 41.5 | 41.9 | 41.9 |
| $H_2O_2$ 50% | 51 | 51 | 51 | 51 |
| Glacial Acetic Acid | 5 | 5 | 5 | 5 |
| Nicotinic acid | | 0.5 | 0.1 | |
| Dipicolinic acid | | | | 0.1 |
| Phosphoric Acid 75% | 2 | 2 | 2 | 2 |
| Total: | 100 | 100 | 100 | 100 |

| Sample | Day | Test | | | | |
|---|---|---|---|---|---|---|
| 40° C. | 7 | $H_2O_2$ | 24.52% | 24.60% | 24.21% | 24.50% |
| 40° C. | 14 | $H_2O_2$ | 23.96% | 25.04% | 24.71% | 25.19% |
| 40° C. | 21 | $H_2O_2$ | 24.16% | 25.22% | 25.18% | 25.37% |
| 40° C. | 28 | $H_2O_2$ | 24.01% | 25.32% | 25.13% | 25.84% |
| 40° C. | 7 | POAA | 1.720% | 1.779% | 1.784% | 1.712% |
| 40° C. | 14 | POAA | 1.638% | 1.979% | 1.914% | 1.897% |
| 40° C. | 21 | POAA | 1.543% | 1.879% | 1.876% | 1.872% |
| 40° C. | 28 | POAA | 1.57% | 1.906% | 1.861% | 1.885% |

As depicted in FIG. 1, the Control A does not contain a stabilizing agent and shows a decline in (or loss of) the peroxyacetic acid at 4 weeks of approximately 10% (or 0.2% of the POAA). The 4 week measurement at 40° C. is indicative of 1 year measurement at room temperature. The results demonstrate that all formulations containing dipicolinic acid and nicotinic acid (Formulations A-C) show strong stabilizing effect after 4 weeks at 40° C. with less than 5% loss of the peroxyacetic acid.

Example 2

Based on the results of Example 1, additional peroxycarboxylic acid compositions were evaluated to compare the stabilizing efficacy of niacin to conventional stabilizing agents. The compositions are shown in wt-% in Table 3.

TABLE 3

| | Formulations | | | | |
|---|---|---|---|---|---|
| Raw material | Formula D | Formula E | Formula F | Formula G | Control B |
| DI water | 12.4 | 12.45 | 12.45 | 12.45 | 12.55 |
| Glacial acetic acid | 39 | 39 | 39 | 39 | 39 |
| Phosphoric acid 75% | 0 | 0.85 | 0.85 | 0.85 | 0.85 |
| $H_2O_2$ 50% | 47.6 | 47.6 | 47.6 | 47.6 | 47.6 |
| HEDP | 1 | 0 | 0 | 0 | 0 |
| Picolinic acid | 0 | 0.1 | 0 | 0 | 0 |
| Niacin | 0 | 0 | 0.1 | 0 | 0 |
| Dipicolinic acid | 0 | 0 | 0 | 0.1 | 0 |
| Total: | 100 | 100 | 100 | 100 | 100 |

Figure 2:
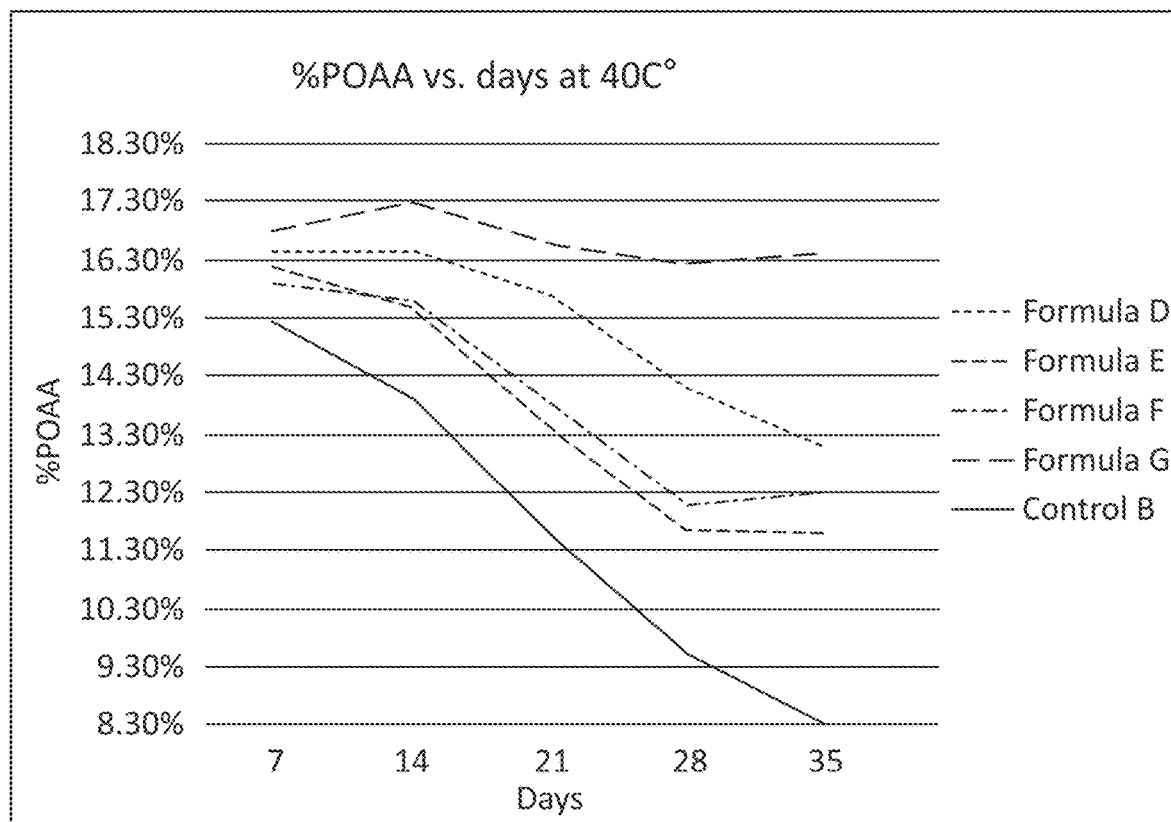
FIG. 2 shows stability of peroxyacetic acid compositions evaluated with various stabilizers.

As depicted in FIG. 2, the Control B does not contain a stabilizing agent and shows a sharp decline in (or loss of) the peroxyacetic acid over time (between 7 days to 35 days) in excess of 40%. The performance of the additional stabilizing agents shows less significant loss of peroxyacetic acid. Formula F in comparison with Control B shows compatible stabilization capability to commonly used stabilizers, such as HEDP.

Example 3

Based on the results of Examples 1 and 2, additional peroxycarboxylic acid compositions having lower concentrations of acetic acid relative to the hydrogen peroxide were evaluated to compare the stabilizing efficacy of niacin to conventional stabilizing agents. The compositions are shown in wt-% in Table 4.

TABLE 4

| | Formulations | | | | |
|---|---|---|---|---|---|
| Raw material | Formula H | Formula I | Formula J | Formula K | Control C |
| DI water | 30 | 30.5 | 30.5 | 30.5 | 30.15 |
| Acetic Acid 100% | 10 | 10 | 10 | 10 | 10 |
| Phosphoric Acid 75% | 0 | 0.85 | 0.85 | 0.85 | 0.85 |
| $H_2O_2$ 50% | 59 | 59 | 59 | 59 | 59 |
| HEDP | 1 | 0 | 0 | 0 | 0 |
| Picolinic acid | 0 | 0.1 | 0 | 0 | 0 |
| Niacin | 0 | 0 | 0.1 | 0 | 0 |
| Dipicolinic acid | 0 | 0 | 0 | 0.1 | 0 |
| Total: | 100 | 100 | 100 | 100 | 100 |

Figure 3:
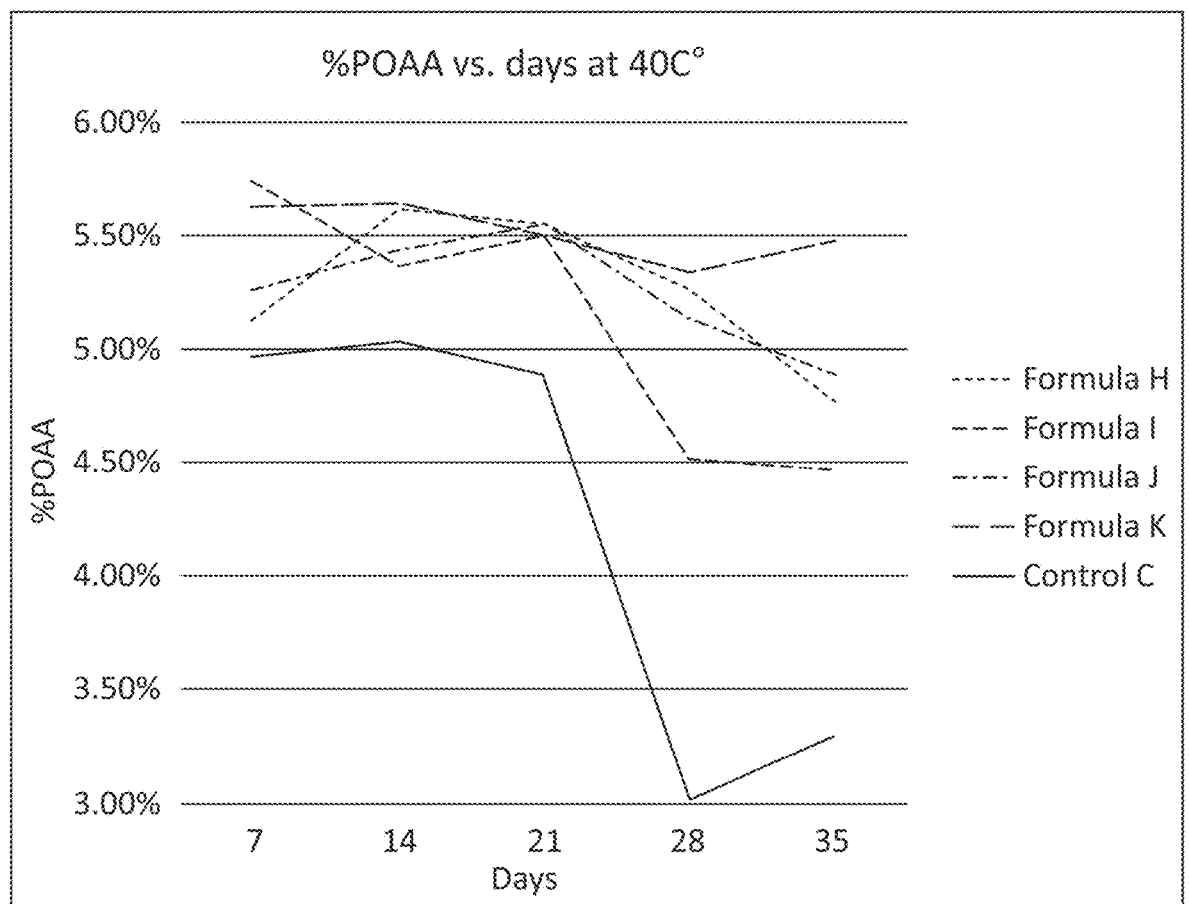
FIG. 3 shows stability of peroxyacetic acid compositions evaluated with various stabilizers.

As depicted in FIG. 3, the control formulation does not contain a stabilizing agent and shows a sharp decline in (or loss of) the peroxyacetic acid over time (between 7 days to 28 days) in excess of 40%. The graph shows an increase at weeks 4-5 which was a result of titration error. The performance of the additional stabilizing agents shows less significant loss of peroxyacetic acid, demonstrating that the use of Niacin as a stabilizing agent is comparable to commonly used stabilizers, such as HEDP and DPA.

Example 4

Additional evaluations of stabilizing agents were conducted for the combination of nicotinic acid and hydroxyethylene diphosphonate (HEDP). The compositions are shown in wt-% in Table 5.

TABLE 5

| Raw material | Formulations | | |
|---|---|---|---|
| | Control D | Formula L | Formula M |
| Acetic Acid 100% | 39 | 39 | 39 |
| $H_2O_2$ 50% | 47.6 | 47.6 | 47.6 |
| HEDP (60%) | 1 | 1 | 1 |
| Nicotinic acid | 0 | 0.1 | 0.5 |
| DI water | 12.4 | 12.3 | 11.9 |
| Total: | 100 | 100 | 100 |

Figure 4:
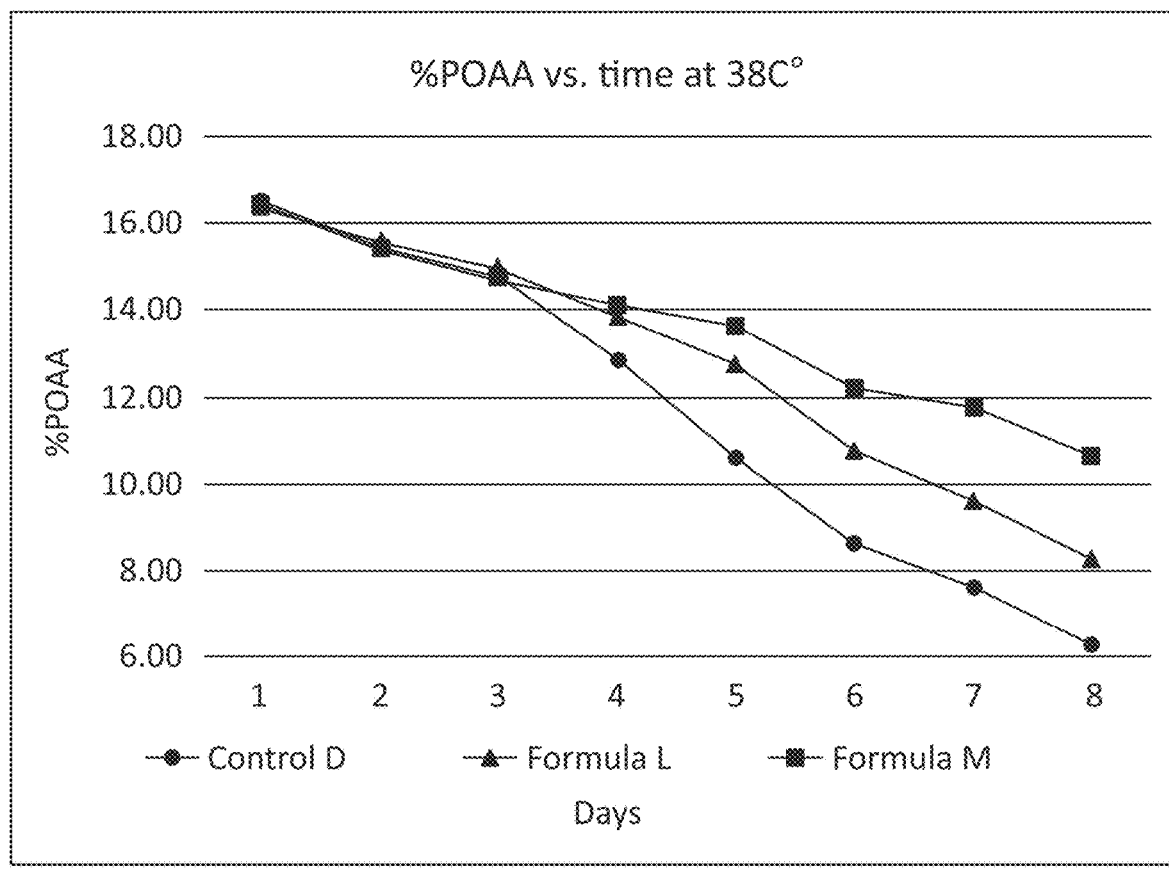
FIG. 4 shows stability of peroxyacetic acid compositions evaluated with a combination of HEDP and additional nicotinic acid stabilizers.

The results in FIG. 4 show a significant improvement of peroxyacetic acid stabilization using blends of nicotinic acid and HEDP on a formulation that is known to be challenging to stabilize. As depicted in FIG. 4, Control D only contains HEDP, whereas Formula L (low niacin) and Formula M (high niacin) contain both HEDP and Nicotinic acid and show an improvement in peroxyacetic acid stabilization. The results are critical to 4 weeks measurement which is indicative to at least 1-year stability.

All publications and patent applications in this specification are indicative of the level of ordinary skill in the art to which this invention pertains. All publications and patent applications are herein incorporated by reference to the same extent as if each individual publication or patent application was specifically and individually indicated by reference. The disclosure of each reference set forth herein is incorporated herein by reference in its entirety. The invention has been described with reference to various specific and preferred embodiments and techniques. However, it should be understood that many variations and modifications may be made while remaining within the spirit and scope of the invention.

What is claimed is:

1. A method of reducing a microbial population on a surface or substrate using a stabilized peroxycarboxylic acid composition comprising:
    providing a peroxycarboxylic acid composition comprising a $C_1$-$C_{22}$ carboxylic acid; a $C_1$-$C_{22}$ peroxycarboxylic acid; hydrogen peroxide, wherein the peroxycarboxylic acid and the hydrogen peroxide are in a weight ratio of from about 2:1 to about 100:1; and a pyridine carboxylic acid comprising nicotinic acid, wherein the composition does not include metal ions and does not include dipicolinic acid; and
    contacting the surface or substrate with a use solution of said composition for sufficient time to reduce the microbial population, wherein said use solution has a pH of or below about 4.

2. The method of claim 1, wherein the surface or substrate is a food item, plant item, animal item, a skin surface, a container, an equipment, a system or a facility for growing, a fermentation equipment or surface, a surface for holding, processing, packaging, storing, transporting, preparing, cooking or serving the food item, plant item or the animal item, an instrument, a hard surface, a liquid media, equipment, a fouled water or industrial processing liquid source, liquid system, or process water used in oil, gas and/or industrial processing operations.

3. The method of claim 1, wherein the microbial population in and/or on the surface or substrate is reduced by at least two log 10.

4. The method of claim 1, wherein the surface or substrate is contacted with about 1 ppm to about 10,000 ppm of the peroxycarboxylic acid, and the contacting of the surface or substrate is by direct contact onto the surface or substrate by a spray, wipe, dip or submersion into the peroxycarboxylic acid composition for a period of at least 10 seconds.

5. The method of claim 1, wherein the peroxycarboxylic acid composition is diluted prior to the contacting.

6. The method of claim 1, wherein the method does not require a rinse step to remove any residual peroxycarboxylic acid composition from the surface or substrate.

7. The method of claim 1, wherein the peroxycarboxylic acid composition exhibits less than 40% loss of peroxycarboxylic acid and/or hydrogen peroxide at a storage temperature of about 40° C. after 4 weeks.

8. The method of claim 1, wherein the peroxycarboxylic acid composition further comprises at least one additional agent comprising an anionic surfactant, a hydrotrope, a defoaming agent, a solvent, a mineral acid, and combinations thereof.

9. The method of claim 1, wherein the peroxycarboxylic acid composition is free of any material that is not considered to be a GRAS (generally recognized as being safe) or food additive ingredient.

10. The method of claim 1, wherein the peroxycarboxylic acid composition further comprises an additional stabilizing agent comprising a phosphonate, phosphate and/or phosphonic acid.

11. The method of claim 10, wherein the additional stabilizing agent is 1-hydroxyethylidene-1, 1-diphosphonic acid (HEDP).

12. The method of claim 10, wherein the additional stabilizing is present in the amount of from about 0.01 wt % to about 7 wt % of the composition.

13. The method of claim 11, wherein the pyridine carboxylic acid stabilizing agent reduces the amount of HEDP included in the composition to less than 15 ppm in the use solution.

14. The method of claim 1, wherein the $C_1$-$C_{22}$ peroxycarboxylic acid comprises from about 1 wt % to about 40 wt % of the composition, the $C_1$-$C_{22}$ carboxylic acid comprises from about 1 wt % to about 80 wt % of the composition, the hydrogen peroxide comprises from about 1 wt % to about 80 wt % of the composition, and the stabilizing agent comprises from about 0.01 wt % to about 10 wt % of the composition.

15. The method of claim 1, wherein the peroxycarboxylic acid composition exhibits less than 20% loss of peroxycarboxylic acid and/or hydrogen peroxide at a storage temperature of about 40° C. after 4 weeks.

16. The method of claim 1, wherein the peroxycarboxylic acid composition exhibits less than 10% loss of peroxycarboxylic acid and/or hydrogen peroxide at a storage temperature of about 40° C. after 4 weeks.

\* \* \* \* \*